(12) United States Patent
Kohlhase et al.

(10) Patent No.: US 8,012,460 B2
(45) Date of Patent: Sep. 6, 2011

(54) GEL EMULSIONS IN THE FORM OF O/W EMULSIONS HAVING A HYDROCOLLOID CONTENT

(75) Inventors: Chemals Füller Kohlhase, Hamburg (DE); Stefanie Von Thaden, Hamburg (DE); Andreas Bleckmann, Ahrensburg (DE); Christel Lemm, Buxtehude (DE); Detlef Emeis, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1417 days.

(21) Appl. No.: 10/467,176

(22) PCT Filed: Feb. 13, 2002

(86) PCT No.: PCT/EP02/01474
§ 371 (c)(1), (2), (4) Date: Apr. 13, 2004

(87) PCT Pub. No.: WO02/066007
PCT Pub. Date: Aug. 29, 2002

(65) Prior Publication Data
US 2005/0019350 A1   Jan. 27, 2005

(30) Foreign Application Priority Data
Feb. 16, 2001  (DE) .................................. 101 07 240

(51) Int. Cl.
*A61K 8/73* (2006.01)
*A61K 8/02* (2006.01)
*A61K 31/715* (2006.01)
*A01N 43/04* (2006.01)

(52) U.S. Cl. .......... 424/70.13; 424/401; 514/54; 514/57

(58) Field of Classification Search .................. 424/401, 424/70.13, 424; 524/844–848, 937–944; 514/54, 57
See application file for complete search history.

(56) References Cited

U.S. PATENT DOCUMENTS

| | | | |
|---|---|---|---|
| 5,725,844 A | | 3/1998 | Gers-Barlag et al. |
| 5,780,445 A | * | 7/1998 | Schneider et al. .............. 514/27 |
| 5,788,952 A | | 8/1998 | Gers-Barlag et al. |
| 6,001,341 A | * | 12/1999 | Genova et al. .............. 424/76.1 |

FOREIGN PATENT DOCUMENTS

| | | |
|---|---|---|
| DE | 19802204 | 7/1999 |
| EP | 0747035 | 12/1996 |
| EP | 1055417 | 11/2000 |
| WO | 94/17779 | 8/1994 |

OTHER PUBLICATIONS

English language abstract of DE 198 02 204 A1.
English language abstract of EP 1 055 417 A2.
English language abstract of EP 0 747 035 A2.

* cited by examiner

*Primary Examiner* — Sreeni Padmanabhan
*Assistant Examiner* — Kendra D Carter
(74) *Attorney, Agent, or Firm* — Greenblum & Bernstein, P.L.C.

(57) ABSTRACT

The invention relates to cosmetic preparations in the form of gel emulsions on preparations of the O/W emulsion type having a hydrocolloid content. Said hydrocolloids are selected from the group of preparations based on (i) hydroxyethylcellulose, (ii) xanthan gum, (iii) carbomer. Said preparations further contain (iv) one or more lipids, (v) one or more non-ionic and/or anionic emulsifiers with HLB values between 8 and 16, the overall content of the emulsifiers not exceeding 1.5% by weight.

45 Claims, No Drawings

GEL EMULSIONS IN THE FORM OF O/W EMULSIONS HAVING A HYDROCOLLOID CONTENT

CROSS-REFERENCE TO RELATED APPLICATIONS

The present application is a U.S. National Stage of International Application No. PCT/EP02/01474, filed Feb. 13, 2002, which claims priority under 35 U.S.C. §119 of German Patent Application No. 101 07 240.6, filed Feb. 16, 2001.

BACKGROUND OF THE INVENTION

1. Field of the Invention

The present invention relates to cosmetic and dermatological preparations, in particular those of the oil-in-water type, to processes for their preparation and to their use for cosmetic and medicinal purposes.

2. Discussion of Background Information

The human skin is the largest human organ and performs numerous vital functions. Having an average area of about 2 $m^2$ in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skincare in the cosmetics sense is to strengthen or restore the skin's natural function as a barrier against environmental influences (e.g. dirt, chemicals, microorganisms) and against the loss of endogenous substances (e.g. water, natural fats, electrolytes), and also to assist its horny layer in its natural regeneration ability in cases of existing damage.

If the barrier properties of the skin are impaired, increased resorption of toxic or allergenic substances or attack by microorganisms may result, leading to toxic or allergic skin reactions.

Another aim of skincare is to compensate for the loss by the skin of sebum and water caused by daily washing. This is particularly important if the natural regeneration ability is inadequate. Furthermore, skincare products should protect against environmental influences, in particular against sun and wind, and delay skin aging.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally understood as meaning heterogeneous systems which consist of two liquids, which are usually referred to as phases, and which are immiscible or miscible with one another only to a limited extent. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic character being determined here by the oil.

Gel creams are particularly light products with a low emulsifier and lipid content. They are characterized by the fact that they can be readily distributed on the skin and impart a fresh feel. Following product application, no or only a little residue should remain on the skin. Gel creams usually comprise a relatively high content of hydrophilic thickeners (e.g. carbopols, xanthan gum, hydroxyethylcellulose) for thickening and stabilizing the systems. Since the thickener or the thickener system is present in the external phase, it has a significant influence on the sensory properties of the product. Current thickener systems can either not be distributed readily, do not produce a fresh feeling or leave behind an excessively greasy residue on the fingers and/or a harsh, sticky feel on the skin after the product has been distributed on the skin.

SUMMARY OF THE INVENTION

The aim was to overcome these disadvantages.

Surprisingly, it has been found that cosmetic preparations in the form of gel emulsions, namely preparations based on preparations of the O/W emulsion type with a content of
hydrocolloids chosen from the group
(i) hydroxyethylcellulose
(ii) xanthan gum
(iii) carbomer,
where the ratio of (i): (ii): (iii) is chosen as a: b: c, where a, b and c, independently of one another are rational numbers from 1 to 5, preferably from 1 to 3, and where in particular b can also assume the value zero,
where (i), (ii) and (iii) are present in the preparations in total concentrations (a+b+c) of 0.25-1.5% by weight, based on the total weight of the preparation, preferably in total concentrations of 0.5-1.0% by weight,
where these preparations further comprise
(iv) one or more lipids,
where the total content of the lipids is chosen from the concentration range from 3.0 to 20.0% by weight, based on the total weight of the preparations, preferably in total concentrations of from 7.5 to 15% by weight,
where these preparations further comprise
(v) one or more nonionic and/or anionic emulsifiers with HLB values between 8 and 16, preferably between 10 and 12
where the total content of the emulsifiers does not exceed 1.5% by weight and is preferably chosen from the concentration range from 0.5 to 1.0% by weight, based on the total weight of the preparations,
achieve these objects.

Accordingly, the present invention provides a composition in the form of a gel emulsion, wherein the composition is based on an O/W emulsion and comprises the following components:
(i) hydroxyethylcellulose;
(ii) xanthan gum;
(iii) carbomer;
(iv) one or more lipids; and
(v) one or more nonionic and/or anionic emulsifiers having HLB values of from 8 to 16, preferably of from 10 to 12.

The ratio of (i): (ii): (iii) is a: b: c and a, b and c independently are numbers of from 1 to 5, preferably of from 1 to 3, and b may additionally be equal to 0. In the composition, components (i), (ii) and (iii) are present in a total concentration of from 0.25% to 1.5% by weight, preferably of from 0.5% to 1.0% by weight. Component (iv) is present in a concentration of from 3.0% to 20.0% by weight, preferably of from 7.5% to 15% by weight. Component (v) is present in a concentration not exceeding 1.5% by weight, preferably in a concentration of from 0.5% to 1.0% by weight. All of these percentages are based on the total weight of the composition.

In one aspect of the composition, component (v) may comprise glyceryl stearate citrate.

In another aspect, the composition may further comprise one or more fatty alcohols, for example, in a concentration of up to 10% by weight, based on the total weight of the composition, preferably in a concentration of up to 5.0% by weight, or in a concentration of up to 3.0% by weight.

In yet another aspect of the composition, component (iv) may comprise less than about 30% by weight of polar lipids and/or may comprise at least one lipid which has an interfacial tension with water of from about 20 to about 30 mN/m.

In a still further aspect, the composition may comprise an emulsion having an oil phase which comprises at least 50% by weight, e.g., at least 75% by weight, of at least one of petrolatum, paraffin oil and polyolefins. Additionally or alternatively, the oil phase may comprise a silicone oil.

In another aspect, the composition may further comprise at least one antioxidant, for example, in a concentration of from 0.001% to 30% by weight, e.g., from 0.05% to 20% by weight or from 1% to 10% by weight, based on the total weight of the composition. The at least one antioxidant may comprise an oil-soluble antioxidant. For example, the antioxidant may comprise vitamin A and/or vitamin E and/or derivatives thereof.

In a further aspect, the composition may comprise vitamin A and/or derivatives thereof in a concentration of from 0.001% to 10% by weight, based on the total weight of the composition, and/or it may comprise vitamin E and/or derivatives thereof in a concentration of from 0.001% to 10% by weight, based on the total weight of the composition.

In a still further aspect, the composition may further comprise at least one UV filter substance which is a UV-A filter substance, a UV-B filter substance and/or an inorganic pigment. For example, the UV filter substance may be present in a total concentration of from 0.1% to 30% by weight, e.g., of from 1.0% to 6.0% by weight, based on the total weight of the composition.

The present invention also provides a cosmetic or dermatological preparation which comprises the composition discussed above, including the various aspects thereof For example, the preparation may be a skin protection cream, a cleansing cream, a cleansing milk, a sunscreen lotion, a nourishing cream, a day cream or a night cream.

The present invention further provides a sunscreen preparation, a lip care product and a hair care product, all of which comprise the composition discussed above.

The present invention also provides an aerosol container which comprises the composition discussed above and a propellant. The propellant may comprise a liquefied hydrocarbon.

The present invention also provides a roll-on device which comprises the above composition.

The present invention also provides method of treating and protecting the skin, wherein the method comprises the application onto the skin of a composition as discussed above, including the various aspects thereof.

It has not been foreseen by the person skilled in the art that the preparations according to the invention
- are more effective moisture-donating preparations,
- are easier to formulate,
- better promote skin smoothing,
- are characterized by better care action,
- are better vehicles for cosmetic and medicinal-dermatological active ingredients,
- would have-better sensory properties, such as, for example, ability to be spread on the skin or the absorption capacity into the skin,
- have greater stability against decomposition in oil and water phases and
- would be characterized by better biocompatibility than the prior art preparations.

The preparations according to the invention therefore represent an enrichment of the prior art.

Xanthan gum (CASE No. 11138-66-2), also called xanthan, represents an anionic heteropolysaccharide which is usually formed by fermentation from corn sugar and is isolated as the potassium salt. It is produced by *Xanthomonas campestris* and a number of other species under aerobic conditions with a molecular weight of $2 \times 10^6$ to $24 \times 10^6$. Xanthan gum is formed from a chain having β-1,4-bonded glucose (cellulose) with side chains. The structure of the subgroups consists of glucose, mannose, glucuronic acid, acetate and pyruvate. Xanthan gum is the name of the first microbial anionic heteropolysaccharide. It is produced from *Xanthomonas campestris* and a number of other species under aerobic conditions with a molecular weight of 2-15 $10^6$. Xanthan gum is formed from a chain having β-1,4-bonded glucose (cellulose) with side chains. The structure of the subgroups consists of glucose, mannose, glucuronic acid, acetate and pyruvate. The number of pyruvate units determines the viscosity of the xanthan gum. Xanthan gum is produced in two-day batch cultures with a yield of 70-90%, based on carbohydrate used. Here, yields of 25-30 g/l are achieved. After the culture has been killed; work-up is carried out by precipitation with, for example, 2-propanol. Xanthan gum is then dried and ground.

Within the scope of the present disclosure, the expression "lipids" is sometimes used as the generic term for fats, oils, waxes and the like, as is entirely familiar to the person skilled in the art. The terms "oil phase" and "lipid phase" are also used synonymously.

Advantageously, the lipid or lipids are chosen from the group of moderately polar to nonpolar llipids. It is preferred to make the proportion by weight of polar lipids in the lipid phase less than about 30%.

Oils and fats differ from one another, inter alia, in their polarity, which is difficult to define. It has already been proposed to adopt the interfacial tension toward water as a measure of the polarity index of an oil or of an oil phase. This means that the lower interfacial tension between this oil phase and water, the greater the polarity of the oil phase in question. According to the invention, the interfacial tension is regarded as one possible measure of the polarity of a given oil component.

The interfacial tension is the force which acts on an imaginary line of one meter in length in the interface between two phases. The physical unit for this interfacial tension is conventionally calculated from the force/length relationship and is usually expressed in mN/m (millinewtons divided by meter). It has a positive sign if it endeavors to reduce the interface. In the converse case, it has a negative sign.

Table 1 below lists moderately polar lipids which are advantageous according to the invention as individual substances or else as mixtures with one another. The relevant interfacial tensions toward water are given in the last column. It is also advantageous in some circumstances to use mixtures of higher and lower polarity and the like, particularly if the overall polarity of the oil phase corresponds to of the moderate or low polarity.

TABLE 1

| Trade name | INCI name | (mN/m) |
|---|---|---|
| Isofol ® 14 T | Butyl Decanol + Hexyl Decanol + Hexyl Octanol + Butyl Octanol | 27.6 |

TABLE 1-continued

| Trade name | INCI name | (mN/m) |
|---|---|---|
| Isofol ® 16 | Hexyl Decanol | 24.3 |
| Eutanol ® G | Octyldodecanol | 24.8 |
| Cetiol ® OE | Dicaprylyl Ether | 22.1 |
| Miglyol ® 812 | Caprylic/Capric Triglyceride | 21.3 |
| Cegesoft ® C24 | Octyl Palmitate | 23.1 |
| Isopropylstearate | Isopropyl Stearate | 21.9 |
| Estol ® 1540 EHC | Octyl Octanoate | 30.0 |
| Finsolv ® TN | $C_{12-15}$ Alkyl Benzoate | 21.8 |
| Cetiol ® SN | Cetearyl Isononanoate | 28.6 |
| Dermofeel ® BGC | Butylene Glycol Caprylate/Caprate | 21.5 |
| Trivent ® OCG | Tricaprylin | 20.2 |
| MOD | Octyldodecyl Myristate | 22.1 |
| Cosmacol ® ETI | Di-$C_{12-13}$Alkyl Tartrate | 29.4 |
| Miglyol ® 829 | Caprylic/Capric Diglyceryl Succinate | 29.5 |
| Prisorine ® 2036 | Octyl Isostearate | 29.7 |
| Tegosoft ® SH | Stearyl Heptanoate | 28.7 |
| Abil ® Wax 9840 | Cetyl Dimethicone | 25.1 |
| Cetiol ® LC | Coco-Caprylate/Caprate | 24.8 |
| IPP | Isopropyl Palmitate | 22.5 |
| Luvitol ® EHO | Cetearyl Octanoate | 28.6 |
| Cetiol ® 868 | Octyl Stearate | 28.4 |

For the purposes of the present invention, the oil phase can also advantageously comprise substances chosen from the group of esters of saturated and/or unsaturated, branched and/or unbranched alkanecarboxylic acids having a chain length of from 3 to 30 carbon atoms, and saturated and/or unsaturated, branched and/or unbranched alcohols having a chain length of from 3 to 30 carbon atoms and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, such as, for example, jojoba oil.

The oil phase can also be chosen advantageously from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12-18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

If desired, fatty and/or wax components which are to be used in the oil phase—as secondary constituents in a minor amount—can be chosen from the group of vegetable waxes, animal waxes, mineral waxes and petrochemical waxes. Examples which are favorable according to the invention are candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes and microcrystalline waxes.

Other advantageous fatty and/or wax components are chemically modified waxes and synthetic waxes such as, for example, those obtainable under the trade names Syncrowax HRC (glyceryl tribehenate), Syncrowax HGLC ($C_{16-36}$-fatty acid triglyceride) and Syncrowax AW 1C ($C_{18-36}$-fatty acid) from CRODA GmbH, and also montan ester waxes, Sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane.

If desired, the fatty and/or wax components can be present either individually or as a mixture.

Any desired mixtures of such oil and wax components can also be used advantageously for the purposes of the present invention. In some instances, it can also be advantageous to use waxes, for example cetyl palmitate, as the lipid component of the oil phase.

Of the hydrocarbons, paraffin oil, hydrogenated polyolefins (e.g. hydrogenated polyisobutene), squalane and squalene can be used advantageously for the purposes of the present invention.

According to the invention, emulsions which are particularly advantageous are those which are characterized in that the oil phase consists of at least 50% by weight, preferably of more than 75% by weight, of at least one substance chosen from the group consisting of Vaseline (petrolatum), paraffin oil and polyolefins, and of the latter, preference is given to polydecenes.

The oil phase can advantageously additionally have a content of cyclic or linear silicone oils or consist entirely of such oils, although it is preferable to use an additional content of other oil phase components apart from the silicone oil or the silicone oils.

Cyclomethicone (octamethylcyclotetrasiloxane, cyclopentasiloxane and cyclohexasiloxane) can be used advantageously. However, other silicone oils can also be used advantageously for the purposes of the present invention, for example hexamethylcyclotrisiloxane, polydimethylsiloxane and poly(methylphenylsiloxane).

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol and glycerol, and, in particular, one or more thickeners which may advantageously be chosen from the group consisting of silicon dioxide, aluminum silicates.

According to the invention, the carbopol or carbopols can advantageously be chosen, for example, from the carbopol grades from Goodrich (Carbopol 980, 981, 1382, 5984, 2984, EDT 2001 or Pemulen TR2).

The anionic or nonionic emulsifier or emulsifiers can advantageously be chosen from the group of a) partial fatty acid esters and fatty acid esters of polyhydric alcohols and ethoxylated derivatives thereof (e.g. glyceryl monostearate, sorbitan stearate, glyceryl stearyl citrate, sucrose stearate)
b) ethoxylated fatty alcohols and fatty acids
c) ethoxylated fatty amines, fatty acid amides, fatty acid alkanolamides
d) alkylphenol polyglycol ethers (e.g. Triton X)

A preferred emulsifier according to the invention is glyceryl stearate citrate. This is available, for example, under the product name "IMWITOR® 370" from Hüls AG.

Preference is given to preparations which are characterized in that they additionally comprise
(vi) one or more fatty alcohols
where the total content of the fatty alcohol is advantageously chosen from the concentration range from 0 to 10% by weight, preferably from the range from 0 to 5.0% by weight, particularly preferably 0 to 3.0% by weight, in each case based on the total weight of the preparations.

Particularly advantageous preparations are also obtained if antioxidants are used as additives or active ingredients. According to the invention, the preparations advantageously comprise one or more antioxidants. Favorable, but nevertheless optional, antioxidants which may be used are all antioxidants customary or suitable for cosmetic and/or dermatological applications.

It is also advantageous to add antioxidants to the preparations according to the invention. The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, lycopene) and their derivatives, chlorogenic acid and derivatives thereof, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, α-glucosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and its derivatives, mannose and its derivatives, zinc and its derivatives (e.g. ZnO, ZnSO$_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active ingredients which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and its derivatives and vitamin A and its derivatives.

The amount of antioxidants (one or more compounds) in the preparations is preferably from 0.001 to 30% by weight, particularly preferably 0.05-20% by weight, in particular 1-10% by weight, based on the total weight of the preparation.

If vitamin E and/or its derivatives are used as the antioxidant or antioxidants, their respective concentrations are advantageously chosen from the range of 0.001-10% by weight, based on the total weight of the formulation.

If vitamin A or vitamin A derivatives or carotenes or their derivatives are used as the antioxidant or antioxidants, their respective concentrations are advantageously chosen from the range of 0.001-10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a coloring action, thickeners, surface-active substances, emulsifiers, emollients, moisturizers and/or humectants, anti-inflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulfates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others.

Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulfate, zinc sulfate and mixtures thereof.

Corresponding requirements apply mutatis mutandis to the formulation of medicinal preparations.

The gel creams according to the invention can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

Accordingly, for the purposes of the present invention, cosmetic or topical dermatological compositions can, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), Which can be used alone or in a mixture with one another. Compressed air is also used advantageously.

The person skilled in the art is of course aware that there are propellants which are nontoxic per se which would be suitable in principle for realizing the present invention in the form of aerosol preparations, but which must nevertheless be avoided because of their unacceptable impact on the environment or other accompanying circumstances, in particular fluorocarbons and chlorofluorocarbons (CFCs).

Also favorable are cosmetic and dermatological preparations which are in the form of a sunscreen. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;
4-aminobenzoic acid derivatives, preferably 2-ethylhexyl 4-(dimethylamino)benzoate, amyl 4-(dimethylamino) benzoate;
esters of cinnamic acid, preferably 2-ethylhexyl 4-methoxycinnamate, isopentyl 4-methoxycinnamate;
esters of salicylic acid, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, 2,2'-dihydroxy-4-methoxy-benzophenone;
esters of benzalmalonic acid, preferably di(2-ethylhexyl) 4-methoxybenzalmalonate;
derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminum, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and their ethers, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

DETAILED DESCRIPTION OF THE INVENTION

The examples below are intended to illustrate the present invention without limiting it.

EXAMPLES

|  | % by wt. |
|---|---|
| (1) Gel cream | |
| Glyceryl stearate citrate | 1.00 |
| Hydrogenated coconut fatty acid glycerides | 1.00 |
| Dicaprylyl carbonate | 3.00 |
| Hydroxyethylcellulose | 0.375 |
| Xanthan gum | 0.125 |
| Carbomer | 0.125 |
| Dimethicone | 3.00 |
| NaOH | 0.31 |
| Hydrogenated polyisobutene | 3.00 |
| Glycerol | 5.00 |
| Perfume | qs |
| Preservative | qs |
| Water | 100.00 |

-continued

| | % by wt. |
|---|---|
| (2) Gel lotion | |
| Glyceryl stearate citrate | 1.00 |
| Hydrogenated coconut fatty acid glycerides | 0.50 |
| Dicaprylyl carbonate | 1.00 |
| Hydroxyethylcellulose | 0.25 |
| Carbomer | 0.15 |
| Cyclomethicone | 5.00 |
| NaOH | 0.10 |
| Hydrogenated polyisobutene | 5.00 |
| Glycerol | 12.00 |
| Perfume | qs |
| Preservative | qs |
| Water | 100.00 |

What is claimed is:

1. A composition which is present as a gel emulsion, wherein the composition is based on an O/W emulsion and comprises the following components:
   (i) hydroxyethylcellulose;
   (ii) xanthan gum;
   (iii) carbomer;
   (iv) one or more lipids; and
   (v) one or more emulsifiers having HLB values of from 8 to 16, said emulsifiers
   comprising at least one of a nonionic and an anionic emulsifier;
   wherein a ratio of (i): (ii): (iii) is a: b: c and a, b and c independently are numbers of from 1 to 5; components (i), (ii) and (iii) are present in a total concentration of from 0.25% to 1.5% by weight, component (iv) is present in a concentration of from 3.0% to 20.0% by weight, and component (v) is present in a concentration not exceeding 1.5% by weight, all percentages being based on a total weight of the composition.

2. The composition of claim 1, wherein a, b and c independently are numbers of from 1 to 3.

3. The composition of claim 2, wherein components (i), (ii) and (iii) are present in a total concentration of from 0.5% to 1.0% by weight.

4. The composition of claim 1, wherein component (iv) is present in a concentration of from 7.5% to 15% by weight.

5. The composition of claim 1, wherein the one or more emulsifiers (v) comprise one or more emulsifiers having HLB values of from 10 to 12.

6. The composition of claim 1, wherein component (v) is present in a concentration of from 0.5% to 1.0% by weight.

7. The composition of claim 6, wherein component (v) comprises glyceryl stearate citrate.

8. The composition of claim 1, wherein the composition further comprises (vi) one or more fatty alcohols.

9. The composition of claim 8, wherein component (vi) is present in a concentration of up to 10% by weight, based on the total weight of the composition.

10. The composition of claim 8, wherein component (vi) is present in a concentration of up to 5.0% by weight.

11. The composition of claim 8, wherein component (vi) is present in a concentration of up to 3.0% by weight.

12. The composition of claim 4, wherein component (iv) comprises less than about 30% by weight of polar lipids.

13. The composition of claim 4, wherein component (iv) comprises at least one lipid which has an interfacial tension with water of from about 20 to about 30 mN/m.

14. The composition of claim 1, wherein the composition comprises an emulsion having an oil phase which comprises at least 50% by weight of at least one of petrolatum, paraffin oil and polyolefins.

15. The composition of claim 14, wherein the oil phase comprises at least 75% by weight of at least one of petrolatum, paraffin oil and polyolefins.

16. The composition of claim 1, wherein the composition comprises an emulsion having an oil phase which comprises a silicone oil.

17. The composition of claim 1, wherein the composition further comprises at least one antioxidant.

18. The composition of claim 17, wherein the at least one antioxidant is present in a concentration of from 0.001% to 30% by weight, based on the total weight of the composition.

19. The composition of claim 3, wherein the composition further comprises at least one antioxidant in a concentration of from 0.05% to 20% by weight, based on the total weight of the composition.

20. The composition of claim 1, wherein the composition further comprises at least one antioxidant in a concentration of from 1% to 10% by weight, based on the total weight of the composition.

21. The composition of claim 18, wherein the at least one antioxidant comprises an oil-soluble antioxidant.

22. The composition of claim 17, wherein the at least one antioxidant comprises at least one of vitamin A and derivatives thereof.

23. The composition of claim 22, wherein the at least one of vitamin A and derivatives thereof is present in a concentration of from 0.001% to 10% by weight, based on the total weight of the composition.

24. The composition of claim 17, wherein the at least one antioxidant comprises at least one of vitamin E and derivatives thereof.

25. The composition of claim 24, wherein the at least one of vitamin E and derivatives thereof is present in a concentration of from 0.001% to 10% by weight, based on the total weight of the composition.

26. The composition of claim 1, wherein the composition further comprises at least one UV filter substance which is at least one of a UV-A filter substance, a UV-B filter substance and an inorganic pigment.

27. The composition of claim 26, wherein the at least one UV filter substance is present in a total concentration of from 0.1% to 30% by weight, based on the total weight of the composition.

28. A composition which is present as a gel emulsion, wherein the composition is based on an O/W emulsion and comprises the following components:
   (i) hydroxyethylcellulose;
   (ii) xanthan gum;
   (iii) carbomer;
   (iv) one or more lipids;
   (v) one or more emulsifiers having HLB values of from 10 to 12, said emulsifiers comprising at least one of a nonionic and an anionic emulsifier; and
   (vi) one or more fatty alcohols;
   wherein a ratio of (i): (ii): (iii) is a: b: c and a, b and c independently are numbers of from 1 to 3; components (i), (ii) and (iii) are present in a total concentration of from 0.5% to 1.0% by weight, component (iv) is present in a concentration of from 7.5% to 15% by weight, component (v) is present in a concentration of from 0.5% to 1.0% by weight, and component (vi) is present in a concentration of up to 3.0% by weight, all percentages being based on a total weight of the composition.

29. The composition of claim 28, wherein component (v) comprises glyceryl stearate citrate.

30. The composition of claim 28, wherein component (iv) comprises less than about 30% by weight of polar lipids.

31. The composition of claim 28, wherein the composition further comprises at least one antioxidant in a concentration of from 1% to 10% by weight, based on the total weight of the composition.

32. The composition of claim 31, wherein the at least one antioxidant comprises at least one of vitamin A, vitamin E and derivatives thereof.

33. The composition of claim 28, wherein the composition further comprises at least at least one of a UV-A filter substance, a UV-B filter substance and an inorganic pigment in a total concentration of 1.0% to 6.0% by weight, based on the total weight of the composition.

34. A cosmetic preparation which comprises the composition of claim 1.

35. The cosmetic preparation of claim 34, which comprises one of a skin protection cream, a cleansing cream, a cleansing milk, a sunscreen lotion, a nourishing cream, a day cream and a night cream.

36. A dermatological preparation which comprises the composition of claim 1.

37. A sunscreen preparation which comprises the composition of claim 26.

38. A lip care product which comprises the composition of claim 1.

39. A hair care product which comprises the composition of claim 1.

40. An aerosol container which comprises the composition of claim 1 and a propellant.

41. The aerosol container of claim 40, wherein the propellant comprises a liquefied hydrocarbon.

42. A roll-on device which comprises the composition of claim 1.

43. A method of treating and protecting skin, wherein the method comprises an application onto the skin of a composition which is present as a gel emulsion, is based on an O/W emulsion and comprises the following components:
 (i) hydroxyethylcellulose;
 (ii) xanthan gum;
 (iii) carbomer;
 (iv) one or more lipids; and
 (v) one or more emulsifiers having HLB values of from 10 to 12, said
 emulsifiers comprising at least one of a nonionic and an anionic emulsifier;
 wherein a ratio of (i): (ii): (iii) is a: b: c and a, b and c independently are numbers of from 1 to 3; components (i), (ii) and (iii) are present in a total concentration of from 0.25% to 1.5% by weight, component (iv) is present in a concentration of from 3.0% to 20.0% by weight, and component (v) is present in a concentration not exceeding 1.5% by weight, all percentages being based on a total weight of the composition.

44. The composition of claim 43, wherein component (v) comprises glyceryl stearate citrate.

45. The composition of claim 44, wherein component (iv) comprises less than about 30% by weight of polar lipids.

\* \* \* \* \*